United States Patent
Xia

(10) Patent No.: US 6,316,224 B1
(45) Date of Patent: *Nov. 13, 2001

(54) CHLORELLA VIRUS PROMOTERS

(75) Inventor: Yuannan Xia, Lincoln, NE (US)

(73) Assignee: Bionebraska, Inc., Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/400,541

(22) Filed: Sep. 21, 1999

Related U.S. Application Data

(63) Continuation-in-part of application No. PCT/US98/05655, filed on Mar. 21, 1998, which is a continuation-in-part of application No. 08/821,559, filed on Mar. 21, 1997, now Pat. No. 5,846,774.

(51) Int. Cl.$^7$ ............................ C12P 12/02; C07H 21/04; C12N 1/21; C12N 5/10; C12N 15/63
(52) U.S. Cl. ................... 435/69.1; 435/243; 435/252.3; 435/252.33; 435/320.1; 435/325; 435/410; 536/24.1
(58) Field of Search ..................... 536/24.1; 435/328.1, 435/325, 410, 243, 69.1, 252.3, 252.33

(56) References Cited

U.S. PATENT DOCUMENTS

| | | |
|---|---|---|
| 4,912,046 | 3/1990 | Henner et al. . |
| 4,952,496 | 8/1990 | Rosenberg et al. . |
| 5,436,128 | 7/1995 | Harpold et al. . |
| 5,563,328 | 10/1996 | Mitra et al. . |
| 5,595,887 | 1/1997 | Coolidge et al. . |
| 5,846,774 | * 12/1998 | Xia ....................................... 435/69.1 |

OTHER PUBLICATIONS

A. Mitra et al. "A Chlorella virus gene promoter functions as a strong promoter both in plants and bacteria," Academic Press, New York, NY, *Biochem Biophys Res Commun*, 204(1): 187–94 (1994).

Y. Xia et al. "Adenine DNA methyltransferase M.CviR1 expression accelerates apoptosis in baculovirus–infected insect cells,"Academic Press, New York, NY, *Virology*, 196(2): 817–24 (1993).

M. V. Graves et al. "Characterization of the gene encoding the most abundant in vitro translation product from virus–infected Chlorella–like algae," Elsevier Science Publishers B. V., New York, NY, *Gene*, 113(2): 149–55 (1992).

DeBoer, et al. *Proc. Nat'l Acad. Sci. USA*, 80:21–25, (Jan. 1983), "The tac promoter: A functional hybrid derived from the trp and lac promoters".

Gruber, et al. 1993, "Vectors for Plant Transformation", In: *Methods in Plant Molecular Biology and Biotecnology*, Glick and Thompson, eds., CRC Press, Inc. Boca Raton, pp 89–119.

Horsch, et al. *Science*, 227:1229–31, (Mar. 8, 1985), "A Simple and General Method for Transferring Genes into Plants".

Itakura, et al. *Science*, 198:1056–1063, (Dec. 9, 1977), "Expression in *Escherichia coli* of a Chemically Synthesized Gene for the Hormone Somatostatin".

Lu, et al. *Virology*, 206:339–352, (1995), "Analysis of 45 kb of DNA Located at the Left End of the Chlorella Virus PBCV–1 Genome".

W. R. McClure *Ann Rev. Biochem.* 54:171–204, (1985), "Mechanism and Control of Transcription Initiation in Prokaryotes".

Miki, et al. 1993, "Procedure for Introducing Foreign DNA Into Plants", In: *Methods in Plant Molecular Biology and Biotechnology*, Glick and Thompson, eds., CRC Press, Inc. Boca Raton, pp. 67–88.

Mitra, et al. *Plant Molecular Biology* 26:85–93 (May 1994), "The Chlorella virus adenine methyltransferase gene promoter is a strong promoter in plants".

Narva, et al. *Nucleic Acids Research* 15(23):9807–9823 (1987), "Molecular cloning and characterization of the gene encoding the DNA methyltransferase, M.CviBIII, from Chlorella virus NC–1A".

M. C. O'Neill *The Journal of Biological Chemistry*, 264(10):5522–5530 (Apr. 5, 1989), "*Escherichia coli* Promoters".

Stefan, et al. *Nucleic Acids Research*, 19(2):307–311 (1991), "Molecular cloning and characterization of the gene encoding the adenine methyltransferase M. CviRI from Chlorella virus XZ–6E".

Swaminathan, et al. *Nucleic Acids Research*, 24(13):2463–2469 (May 14, 1996), "Molecular cloning of the three restriction endonuclease R.CviJI from eukaryotic *Chlorella* virus IL–3A".

Van Etten, et al. *Gene*, 74:113–115 (Jun. 20, 1988),"*Chlorella* viruses code for restriction and modification enzymes".

Van Etten, et al. *Microbiological Reviews*, 55(4):586–620 (Dec. 1991), Viruses and Viruslike Particles of Eukaryotci Algae.

Van Etten, *Mol. Cells*, 5(2):99–106 (1995), "Giant *Chlorella* Viruses".

Xia, et al. *Molecular and Cellular Biology*, 6(5): 1430–1439, "Restriction Endonuclease Activity Induced by PBCV–1 Virus Infection of Chlorella–Like Green Alga".

Xia, et al. *Molecular and Cellular Biology*, 6(5):1440–1445 (May 1986), "DNA Methyltransferase Induced by PBCV–1 Virus Infection of a *Chlorella* –Like Green Alga".

\* cited by examiner

*Primary Examiner*—Terry McKelvey
(74) *Attorney, Agent, or Firm*—Foley & Lardner

(57) ABSTRACT

The present invention provides novel promoter sequences obtained from Chlorella virus. The invention includes gene constructs comprising a promoter sequence of the invention operably linked to a DNA sequence encoding a structural gene. The invention also provides vectors and host cells for expressing product encoded by the structural gene of a gene construct of the invention amd cells transformed with the heterologous gene operably linked to the promoter.

23 Claims, 9 Drawing Sheets

Plasmid map of the pBN115-glp expression vector. The construction of the vector plasmid is described in the text. Symbols: ori, pBR322 replication origin. lac Iq, lac I repression gene. ApR, ampicillin resistance gene. 8cGLP, 8 copy GLP-1 gene. YX-15, the YX-15 promoter.

FIG. 6

Comparison of expression of GLP-1 from pBN115-glp and pBN115-glp/tac at various temperatures. E. coli HMS174 containing pBN115-glp (lanes 1-4) and pBN115-glp/tac (lanes 5-8) was grown in the absence (lanes 1 and 5) and presence (lanes 2-4 and 6-8) of 1 mM IPTG, at 37°C (lanes 2 and 6), 27°C (lane 3 and 7), or 21°C (lanes 4 and 8) for 15 hours. Cells were then harvested by centrifugation and sonicated. Total cell lysates from a 0.1 OD 600 unit of cells were analyzed on a 16% SDS-polyacrylimade gel in 100 mM Tris, 100 mM Tricine, and 0.1% SDS (pH 8.3). The gel was stained with Coomassie blue. Arrow identifies the GLP-1 polyprotein bands. The relative amounts of the GLP-1 protein are summarized in Table 1. Lane M represents molecular weight standards in kilodaltons.

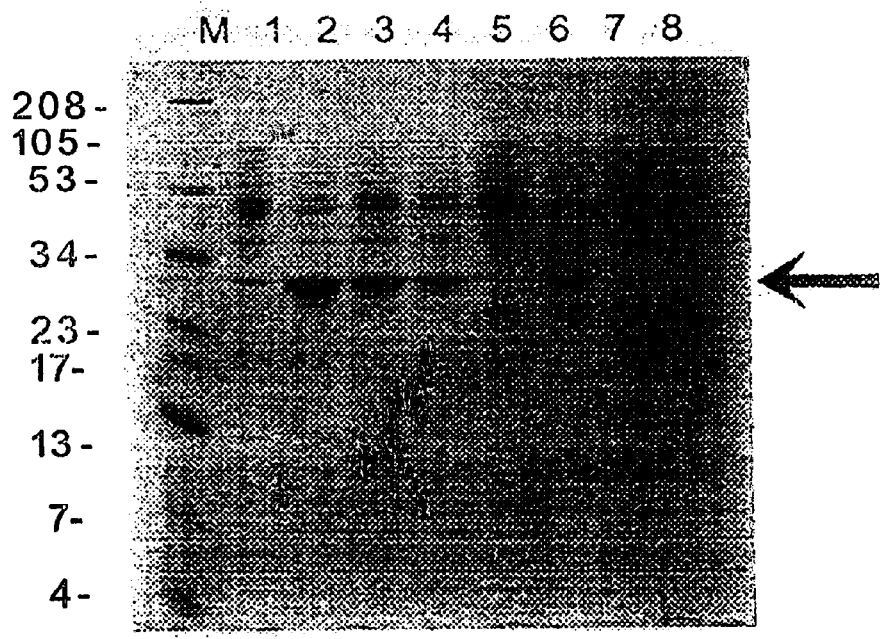

FIG. 7

Tac and YX16 expression of 3 copy GLP(7-36) protein

Lane 1: Novex MW marker
Lane 2: pGEXlnk2 (3 copy GLP) YX16 uninduced total protein, 37 C
Lane 3: pGEXlnk2 (3 copy GLP) YX16 induced total protein, 37 C
Lane 4: pGEXlnk2 (3 copy GLP) YX16 induced total protein, 27 C
Lane 5: pGEXlnk2 (3 copy GLP) YX16 induced soluble protein, 27 C
Lane 6: pBN95lnk2 (3 copy GLP) Tac @ uninduced total protein, 37 C
Lane 7: pBN95lnk2 (3 copy GLP) Tac @ induced total protein, 37 C
Lane 8: pBN95lnk2 (3 copy GLP) Tac @ induced total protein, 27 C
Lane 9: pBN95lnk2 (3 copy GLP) Tac @ induced soluble protein, 27 C @ Full description of this plasmid is pBN95lnk2[GLP(7-36)AFAM]8HAE (tac). The fusion protein is identical in the 3 copy GLP pGEX plasmid from lanes 2-5.

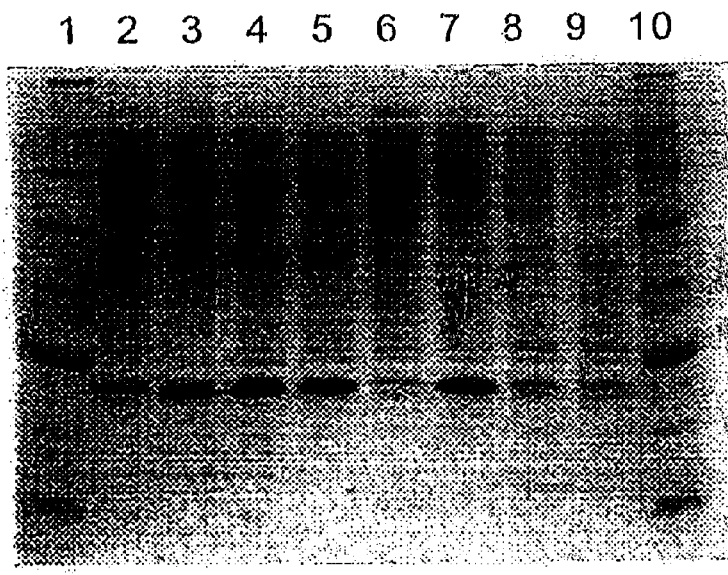

FIG. 8

Tac, YX15 and YX16 expression of 8 copy GLP(7-36) protein

Lane 1: pBN95lnk2[GLP(7-36)AFAM]8HAE (tac) Induced total protein, 37C
Lane 2: pBN95lnk2[GLP(7-36)AFAM]8HAE (tac) Induced total protein, 27C
Lane 3: pBN95lnk2[GLP(7-36)AFAM]8HAE (tac) Induced soluble protein, 27C
Lane 4: pBN53lnk2[GLP(7-36)AFAM]8HAE (YX16) Induced total protein, 37C
Lane 5: pBN53lnk2[GLP(7-36)AFAM]8HAE(YX16) Induced total protein, 27C
Lane 6: pBN53lnk2[GLP(7-36)AFAM]8HAE(YX16) Induced soluble protein, 27C
Lane 7: pBN115-glp (8 copy GLP) (YX15) Induced total protein, 37C
Lane 8: pBN115-glp (8 copy GLP) (YX15) Induced total protein, 27C
Lane 9: pBN115-glp (8 copy GLP) (YX15) Induced soluble protein, 27C
Lane 10: Novex MW marker

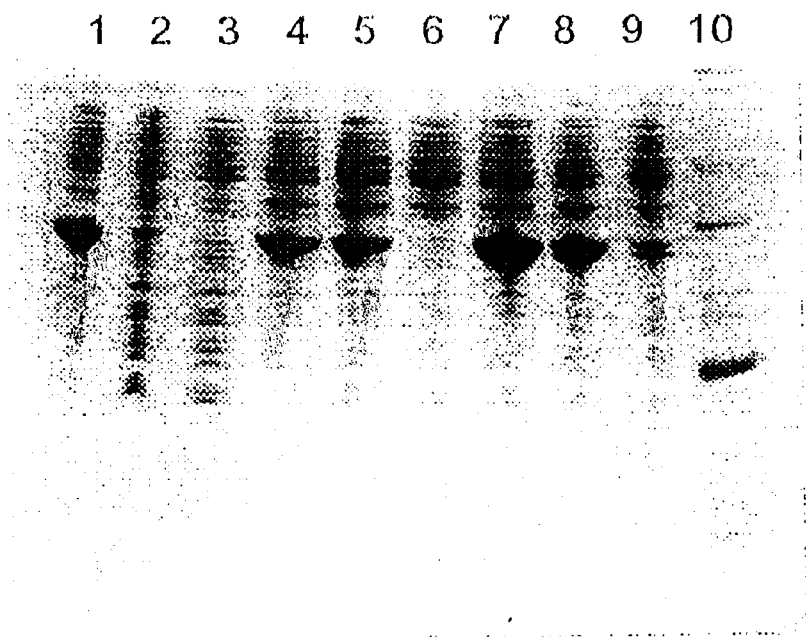

Plasmid name: pBN95lnk2[GLP(7-36)AFAM]8HAE(tac)
Plasmid size: 6685 bp
Constructed by:
Construction date: 6/13/97
Comments/References:

CHLORELLA VIRUS PROMOTERS

This application is a continuation-in-part of International application No. PCT/US98/05655, filed Mar. 21, 1998, which is a continuation-in-part of U.S. application Ser. No. 08/821,559, filed Mar. 21, 1997, now U.S. Pat. No. 5,846,774.

FIELD OF THE INVENTION

This invention relates to novel promoters isolated from Chlorella virus. The novel promoters are useful for expression of heterologous genes in host cells.

BACKGROUND OF THE INVENTION

Genetic engineering allows for isolation of a structural gene from one organism and expression of that gene in a different organism. Expression of a gene includes both transcription of the nucleic acid into mRNA and translation of the mRNA into protein. In order for the structural gene to be expressed in a new organism, the gene must be linked to a regulatory sequence in the proper location to signal transcription of the gene. The regulatory sequence generally includes a promoter sequence upstream from the structural gene. A promoter sequence is a DNA sequence which directs transcription of a structural gene. The nucleic acid sequence of the structural gene is transcribed into messenger RNA (mRNA) and then translated into a sequence of amino acids characteristic of a specific polypeptide or protein. Typically, a promoter sequence is located in the 5' region of a gene, upstream from the transcriptional start site of the structural gene.

A promoter may be inducible or constitutive. In response to an inducing agent, the activity of an inducible promoter is increased, thereby increasing the rate of transcription of an operably linked coding sequence. In contrast, the rate of transcription of a gene under control of a constitutive promoter is not regulated. It is noted, however, that a constitutive promoter can be made an inducible promoter by the addition of an operator sequence. For example, the lac operator is added to the T7 bacteriophage promoter, changing it from a constitutive promoter to one induced by IPTG (Rosenberg, et al., U.S. Pat. No. 4,952,496).

Although not under the control of an inducing agent, some constitutive promoters provide higher levels of transcription than others. High activity promoters providing of high levels of gene transcription can have significant advantage in commercial production of a gene product.

In general, the ability of a promoter to direct transcription outside of its natural host varies. Moreover, the transcription rate of a particular promoter can also vary with the particular host in which the promoter is functioning. Therefore, new promoters capable of promoting high levels of transcription in a wide variety of host cells are needed.

The Chlorella viruses are a group of viruses which infect certain strains of unicellular, eukaryotic, Chlorella-like green algae. (Van Etten, 1995, *Mol. Cells.* 5:99–106; Van Etten, et al., 1991, *Microbiol. Rev.* 55:586–620). These viruses are among the largest and most complex viruses known, generally 150–190 nm diameter polyhedrons containing greater than 300 kb of double stranded DNA. The Chlorella virus genome has the potential to encode several hundred gene products.

Chlorella virus methyltransferase promoters have been isolated and shown to function in prokaryotic and eukaryotic host cell systems. These methyltransferase promoters function well in some bacterial and higher plant cells. See, for example, U.S. Pat. No. 5,563,328; and Mitra, et al., 1994, *Plant Molec. Biol.*, 26: 85–893 ("Mitra").

The present invention provides novel promoter sequences isolated from Chlorella virus that can induce a high level of gene expression in prokaryotic or eukaryotic cells, and over a wide range of temperatures, e.g., about 21° C. to 37° C.

SUMMARY OF THE INVENTION

The present invention provides novel promoter sequences isolated from Chlorella virus (SEQ ID NOS: 1–7). The invention includes gene constructs comprising a promoter sequence of the invention operably linked to a DNA sequence of a structural gene. The invention further provides vectors and host cells for expressing a product encoded by the structural gene of a gene construct of the invention, and cells transformed with a heterologous gene operably linked to the promoter.

The promoters of the invention include inducible Chlorella promoters, rendered inducible, for example, by fusion to an operator sequence. In a preferred embodiment, the Chlorella promoters of the invention are fused to a lac operator. The Chlorella promoters of the invention show very strong promoter activity over a wide range of temperatures, for example, from about 21° C. to about 37° C.

In one embodiment, the structure gene is a non-Chlorella virus DNA sequence encoding a protein for production in a host cell. According to this embodiment, the non-Chlorella virus DNA sequence can be any suitable structural gene which encodes a peptide, protein, hormone, enzyme, etc. Examples of suitable structural genes include glucagon like peptide 1 (GLP-1), growth hormone releasing factor (GRF), parathyroid hormone (PTH), interlinking peptides, amidation code sequences, carbonic anhydrase, beta-galactosidase, chloramphenicol acetyltransferase (CAT), glutathione acetyltransferase, and the like.

A gene construct of the invention is introduced into an appropriate host cell for expression of the gene product. Host cells are transformed directly or through a vector. In one embodiment, a suitable vector for a prokaryotic cell such as *E. coli* strains HB101 or JM109 is the plasmid pKK232-8.

The promoters of the invention are useful in a wide variety of prokaryotic and eucaryotic host cells. In one embodiment, the promoters of the invention are used to promote high levels of gene expression in plants, including tobacco, wheat, and other plants.

The invention further provides a process for producing a protein composition. According to this embodiment, a protein product is produced in a host cell transformed with a gene construct of the invention. The gene construct includes a promoter sequence of the invention operably linked to a structural gene encoding the protein to be produced in the host cell. The invention also provides methods for screening and isolating a promoter sequence having strong transcriptional properties, including truncated versions of the Chlorella virus promoters shown below.

BRIEF DESCRIPTION OF THE DRAWINGS

FIG. 6 is an SDS-PAGE gel showing expression of GLP-1 from pBN115-glp and pBN115-glp/tac at various temperatures.

FIG. 7 is a photograph of an SDS polyacrylatide gel of proteins expressed from expression cassettes containing 3 copy GLP-1 and YX16 promoter or tac promoter, induced and uninduced, soluble and insoluble protein, at 27° C. and 37° C.

FIG. 8 a photograph of an SDS polyacrylamide gel of proteins expressed from expression cassettes fomed with 8 copy GLP-1 and the YX15, YX16, or tac promoter, induced and uninduced, soluble and insoluble protein, at 27° C. and 37° C.

DETAILED DESCRIPTION OF THE INVENTION

Figure 1:
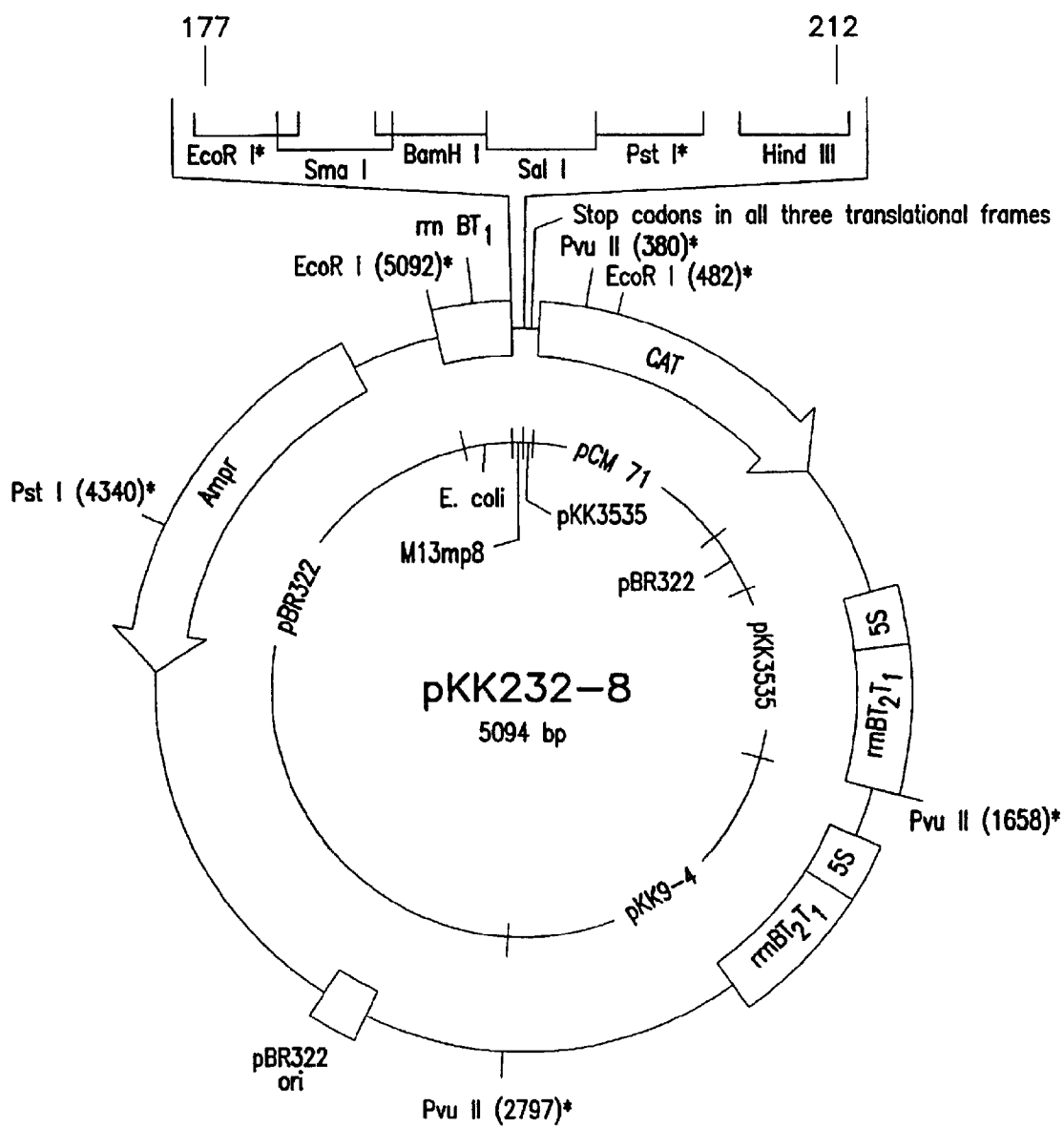
FIG. 1 is a diagrammatic representation of the pKK232-8 plasmid map.

The present invention is directed to novel nucleic acid sequences isolated from the genome of several Chlorella viruses, which isolated nucleic acid sequences fromction as tnanscriptional promoters [SEQ ID NOS: 1–7]. The disclosed promoter sequences are operably linked to a structural gene to direct transcription of the structural gene in prokaryotic or eukaryotic cells. The disclosed promoter sequences provide a high level of gene expression in comparison to native or other non-native promoters, as shown in the examples below in bacterial host cells.

The disclosed promoter sequences are operably linked to a structural gene sequence to form a "gene construct" or "expression cassette". In a typical embodiment, the structural gene sequence of a gene construct will be a heterologous sequence. As used herein, a "heterologous sequence" is a DNA sequence which is different than that to which the promoter sequence is operably linked in the Chlorella virus. The gene construct preferably also includes enhancers, markers, polyadenylation sequences or other regulatory nucleic acid sequences. When a secreted protein is to be produced, the coding sequence of the structural gene preferably includes a nucleic acid sequence encoding a signal peptide.

The disclosed gene constructs are used to express a protein product encoded by the structural gene in host cells. The gene construct is incorporated into the host cells directly or via a vector, using known methods. The protein product remains intracellular post-expression or is secreted extracellularly when a nucleic acid sequence encoding a signal peptide is included in the gene construct.

Chlorella Virus Promoter Sequences

The following nucleic acid sequences were isolated from Chlorella viruses and include a promoter sequence for directing transcription of a structural gene.

cvp-1 [SEQ ID NO: 1]
CCCGGGGATC GCAGGGCATG GGCATTAAAA GAACTTTATG

GAATCAAAAA TCTTAGTGAA TTTCCACCAC AGGTATATAG

TCTTCAGGAC GCTAACGATG ATATCAACGA TTGTATCAAA

GGTTATCGTT TGAGGCACTC ATATCAGGTA GTTTCTACAC

AGAAACTTGA ACAACGCCTG GGAAAAGATC CTGAGCATAG

TAACTTATAT ACTAGCAGAT GTTGTAACGA TGCTTTATAT

GAATATGAAT TAGCACAACG ACAACTACAA AAACAACTTG

ATGAATTTGA CGAAGATGGG TATGATTTTT TTCAGGCACG

TATAAATACA TTAGATCCGT CGACCTGCAG CCAAGCTT cvp-3 [SEQ ID NO: 2]
CCCGGGGATC TAATTCAGGG TGCGAATTTC TTGAACATCA

AAGGTCTGTT GGACGTTTTG TGTGCAGCGG TTGCTGATCG

CATTGAATCC ATCAATAAAC AGATTGGGGT AAATATCAAA

CCCAGTTAGT CGGACATTAG AAGGATTTGT GAGACCACCA

CATCCAACGA CACCTAATGG TGTTGTGAAT GATATATTAG

AAATGTTACT TATCATTGAT ATTTGCATAA CACCATTTCC

CTTTGCTTGA TTTCTACCTA TACTAATTGA TTGTATTGTA

GTGCACGCGG CGTACTTACT TGTATTTGCC GTCTCAGACG

TGCTTGATAA TAGTGTGGAA CTCGAGTATG ATCCGTCGAC

CTGCAGCCAA GCTT cvp-6 [SEQ ID NO: 3]
CCCGGGGATC ATCGAAAGCA ACTGCCGCAT TCGAAACTTC

GACTGCCTCG TTATAAAGGT TAGTGAAAGC CATTGTATGT

TATTACTGAG TTATTTAATT TAGCTTGCTT AAATGCTTAT

CGTGTTGATA TGATAAATGA CAAATGATAC GCTGTATCAA

CATCTCAAAA GATTAATACG AAGATCCGTC GACCTGCAGC

CAAGCTT cvp-10 [SEQ ID NO: 4]
CCCGGGGATC GTTTCTCAGG GCGTCCGGGA GCATATTTCA

GACTTGTCCA GCCGTATGAG CATCACGTGC GCGTTCCTAG

CAAGAGCGTG TACGTATATT CTTTCGCTCT AGAAGATGCA

GATTCGAGAC AACCGAATGG ATCGAATCTA TTTGTACCCC

GATATATATA GAATCTAGTC TAAACAAAAC GACCGCGGCT

CTTGCCAATA AATGTGACGC AATTAACGCA TTCGTGAATG

ATGACTTGTC CGCCCCGGTT CTTGACATTC TAAAAAAATG

TGGAGTATCC TCGATCCGTC GACCTGCAGC CAAGCTT cvp-13 [SEQ ID NO: 5]
CCCGGGGATC TGCGTATTGC GGGACTTTTG AGCATTTTCC

AGAACGGATT GCCGGGACGT ATACTGAACC TCCAGTCCCT

TTGCTCGTCG TATTTCCCAT AATATACATA TACACTATTT

TAATTATTTA CACCGGTTGT TGCTGAGTGA TACAATGCAA

ATTCCCTCCA CCGAGGAGGA TCGCGAACTG TCCAAATGTC

-continued

```
TTCTTTCTGC AGCTCCATAC GGAGTCGTTA GGAAACATTC

ACTTAATTAT AGGATCCGTC GACCTGCAGC CAAGCTT cvp-15 [SEQ ID NO: 6]
CCCGGGGATC AGGCCTCGCT TATAAATATG GTATTGATGT

ACTTGCCGGT GTGATTGACT CAGATTACAG AGGAGAGTTG

AAAGCAATCC TTTACAATAC TACAGAACGT GACTATATTA

TCAAAAAAGG CGATCAGCCA AGCTTCGTCG ACCTGCGATC

CGTCGACCTG CAGCCAAGCT T cvp-16 [SEQ ID NO: 7]
CCCGGGGATC GCAAAACTCA CAGTCAACAA ACCAAAACAC

GGAATGAAGA AAGGAGAAAC TGTGATCATG TGGCAACAAG

ATGGAGGTGT CATAGACTAC ATTTACCCTC CCTCTGATCA

TCGAAAGCAA CTGCCGCATT CGAAACTTCG ACTGCCTCGT

TATAAAGGTT AGTGAAAGCC ATTGTATGTT ATTACTGAGT

TATTTAATTT AGCTTGCTTA AATGCTTATC GTGTTGATAT

GATAAATGAC AAATGATACG CTGTATCAAC ATCTCAAAAG

ATTAATACGA AGATCCGTCG ACCTGCAGCC AAGCTT
```

The method by which these new promoter sequences were discovered is described more fully in the Examples below. Briefly, restriction DNA fragments were generated from the viral genomes of five Chlorella viruses, CA4B, Al-1A, PBCV-1, SC-1A, and NC-1A. (Van Etten, 1991, *Microbiol Rev.* 55:586–620). The restriction fragments were inserted into plasmid pKK232-8 by a shotgun cloning procedure using known methods (Sambrook, et al., 1989, *Molecular Cloning*).

The plasmid vector pKK232-8 contains a promoterless chloramphenicol acetyltransferase (CAT) gene and multiple cloning sites upstream for insertion of DNA restriction fragments. *E. coli* were then transformed with the cloned pKK232-8 and the transformants carrying promoter sequences were screened for resistance to chloramphenicol. To obtain high activity promoters, chloramphenicol-resistant transformants were further screened using increasing concentrations of chloramphenicol 0 in the growth medium.

As used herein, the "strength" of a promoter refers to the level of transcription directed by the promoter. A "strong" promoter provides a greater level of transcription than a weak promoter. Thus, the phrase "strong promoter" is used interchangeably with a "high activity promoter". Strong promoters are particularly useful for commercial production of a gene product.

It is appreciated that the entire nucleic acid sequence recited for each of SEQ ID NOS: 1–7 may not be required for promoter function. Using the methods described above and in the Examples below, the disclosed promoter sequences can be further restricted, e.g. truncated or modified, and screened to refine the active promoter regions.

Preparation of Gene Constructs

According to the invention, a gene construct includes at least one structural gene coding sequence which is operably linked to a transcriptional control region. A transcriptional control region includes promoters, and other regulatory elements, such as enhancers, regulatory elements, polyadenylation sequences, transcriptional initiation regions, and transcriptional termination sequences. SEQ ID NOS: 1–7 each include a promoter sequence and may also include additional regulatory elements. Methods for operably linking a promoter sequence to a structural gene sequence are known and disclosed in, for example, Itakuri, et al., 1977, *Science* 198:1056–1063.

A structural gene of a gene construct according to the disclosure will typically encode a protein or polypeptide product. Any known or later discovered structural gene which encodes a desired product is operably linked to a promoter sequence of the invention using known methods. Examples of known structural genes suitable for use with the promoters of the invention include those nucleic acid sequences encoding: glucagon-like peptide 1 (GLP-1), growth hormone releasing factor (GRF), parathyroid hormone(PTH), carbonic anhydrase, beta-galactosidase, chloramphenicol acetyltransferase (CAT), glutathione acetyltransferase, interlinking peptides, amidation sequences, and the like structural genes.

Therefore, in one embodiment, a promoter sequence of the invention is operably linked to a DNA sequence encoding carbonic anhydrase, for example, human carbonic anhydrase. In another embodiment, a promoter sequence of the invention is linked to a DNA sequence encoding multiple copies of a desired protein. An example of a suitable multiple copy structural gene for glucagon like peptide-1 (GLP-1) iis disclosed in U.S. Pat. No. 5,595,887.

Gene Transformation Method

Once a gene construct is formed, it is introduced into a host cell directly or subcloned into an appropriate vectorfor transforming a host cell.

Methods of transforming cells are known, and the preferred method varies with the type of host cell to be transformed. As used herein, a "host cell" refers to the cell in which the structural gene of the gene construct is ultimately expressed. For prokaryotic and eukaryotic host cells, including bacterial, yeast, and animal host cells, preferred methods of transformation include methods of freeze/thaw, calcium chloride precipitation, calcium phosphate precipitation, plasmids, protoplast transformation, liposome mediated transformation, electroporation, and other known transformation methods.

For plant cells, preferred methods of transformation include Agrobacterium-mediated transformation, electroporation, microparticle bombardment, protoplast fusion, combinations of these and other known transformation methods.

Host Cells

The promoters of the invention are useful in a wide variety of host cells, including procaryotic and eucaryotic host cells. Suitable bacterial host cells for expression of a gene construct of the invention include *Escherichia coli*, *Bacillus subtilis* and Streptomyces. Plant and animal host cells, including yeast cells, such as tobacco, wheat and other plant cells, embryonic, tumor, and other animal cells, and the like, are also useful with the inventive promoters.

Suitable vector systems for carrying the gene constructs into the host cells include, for example, plasmids, viruses, phages, and yeast artificial chromosomes (YAC's). Suitable plasmids for transforming a bacterial host cell with a gene construct of the invention include pKK232-8 or pB0304, as described in the examples below.

Methods for introducing foreign genes into plants are known and can be used to insert a gene construct of the invention into a plant host, including biological and physical plant transformation protocols. See, for example, Miki, et al., 1993, "Procedure for Introducing Foreign DNA Into Plants", In: *Methods in Plant Molecular Biology and Biotechnology*, Glick and Thompson, eds., CRC Press, Inc., Boca Raton, pages 67–88. The methods chosen vary with the host plant, and include chemical transfection methods such as calcium phosphate, microorganism-mediated gene transfer such as Agrobacterium (Horsch, et al., *Science* 227:1229–31, 1985), electroporation, micro-injection, and biolistic bombardment.

Expression vectors and in vitro culture methods for plant cell or tissue transformation and regeneration of plants are known and available. See, for example, Gruber et al., 1993, "Vectors for Plant Transformation: In: *Methods in Plant Molecular Biology and Biotechnology,* Glick and Thompson, eds., CRC Press, Inc., Boca Raton, pages 89–119.

EXAMPLES

The invention is more fully described with reference to the following examples, which are not intended to limit the invention in any way.

Example 1

Generating Viral DNA Fragments

Viral DNA extracted from five Chlorella viruses CA-4B; Al-1A; PBCV-1; SC-1A; and NC-1A was provided by Dr. Van Etten at the University of Nebraska. The extracted viral DNA (1.5 μg of each) was pooled and viral DNA fragments were generated by digestion with Sau3A1(New England Biolabs, Beverly, Mass.) in (100 μl volume) 100 mM NaCl, 10 mM Bis Tris Propane-HCl, 10 mM $MgCl_2$, 1 mM dithiothreitol, and 100 μg/ml BSA. The mixture was incubated at 37° C. for 120 minutes and stopped by 10 mM EDTA. Sau3A1 fragments were precipitated from the digestion mixture by ethanol and washed with ethanol.

Example 2

Cloning Fragments into pKK232-8

The Sau3A1 viral fragments produced as described for Example 1, were cloned into plasmid pKK232-8 at the single BamHI site by a shotgun cloning procedure as described in Sambrook, et al., 1989, *Molecular Cloning.* Plasmid pKK232-8 was purchased from Pharmacia (Piscataway, N.J.). The map of pKK232-8 is diagrammatically represented in FIG. 1. Preparations of DNA, fill-in reaction and ligations were carried out as described in Sambrook et al., supra or according to the manufacturer's directions.

The Chlorella viral DNA fragments were ligated to 1 μg of pKK232-8 which was previously treated with BamHI and calf intestinal alkaline phosphatase (CIP) to yield recombinant plasmids pCVP-1; pCVP-3; pCVP6; pCVP-10; pCVP-13; pCVP-15; and pCVP-16. The seven Chlorella virus promoters operably linked to a heterologous CAT gene are diagrammatically shown in FIG. 2. (Abbreviations: Sm, SmaI; Sa, SalI H, HindIII; CAT, chloramphenicol acetyltransferase gene), Calf intestinal alkaline phosphatase was purchased from Promega (Madison, Wis.). T4 DNA ligase was purchased from BRL (Rockville, Md.).

pKK232-8 is a derivative of pBR322 which contains promotorless chloramphenicol acyltransferase (CAT) gene and multiple cloning sites upstream for insertion of DNA restriction fragments. *E. coli* cells transformed with pKK232-8 are resistant to ampicillin but sensitive to chloramphenicol unless a DNA fragment containing a promoter is inserted upstream of the CAT gene to induce expression of CAT. If such a promoter is inserted, cells carrying the recombinant plasmid express CAT and thereby acquire resistance to chloramphenicol.

pKK232-8 is designed to reduce background of chloramphenicol resistance and increase the capacity of screening strong promoters. To reduce background, the CAT gene is flanked by efficient transcription terminators that block transcription into the CAT gene from other promoters present on the plasmid. Translational stop codons are introduced in all three reading frames between the multiple cloning sites and the initiation codon of the CAT gene to prevent translational readthrough from any ATG start codon that might be introduced by the cloned promoter fragment. The CAT gene also contains its own ribosome-binding signal and ATG start codon to allow efficient translation from CAT mRNA.

Example 3

Transformnation of *E. coli* and Selection of Transformants

Transformation of *E. coli* strains HB101 and JM109 was performed as described by Sambrook, et al., 1989, supra. The *E. coli* strains were purchased from Promega (Madison, Wis.).

Transformed *E. coli* were screened for resistance to ampicillin indicating transformation with pKK232-8, and for resistance to chloramphenicol, indicating insertion of a promoter. The strength of an inserted promoter was estimated by measuring cell growth in the presence of increasing amounts of chloramphenicol.

Positive colonies were isolated on Luria Broth (LB) plates containing 30 μg/ml ampicillin and various concentrations of chloramphenicol (5, 10, 20, 30, 100 μg/ml). *E. coli* colonies which were resistant to 100 μg/ml chloramphenicol were selected and inoculated into LB medium containing 200, 400, 600, 700, 900 μg/ml chloramphenicol. Cell growth was monitored by measuring $OD_{600}$ of cultures.

Several thousand transformants, resistant to 30 μg/ml chloramphenicol, were obtained. The number of transformants resistant to chloramphenicol dramatically decreased with increased concentration of the antibiotic. Only about 500 transformants were resistant to 100 μg/ml chloramphenicol and only 36 transformants showed resistance to 500 μg/ml chloramphenicol. Cells transformed with control pKK232-8 without an inserted promoter were not resistant to chloramphenicol above a concentration of 5 μg/ml.

Figure 2:
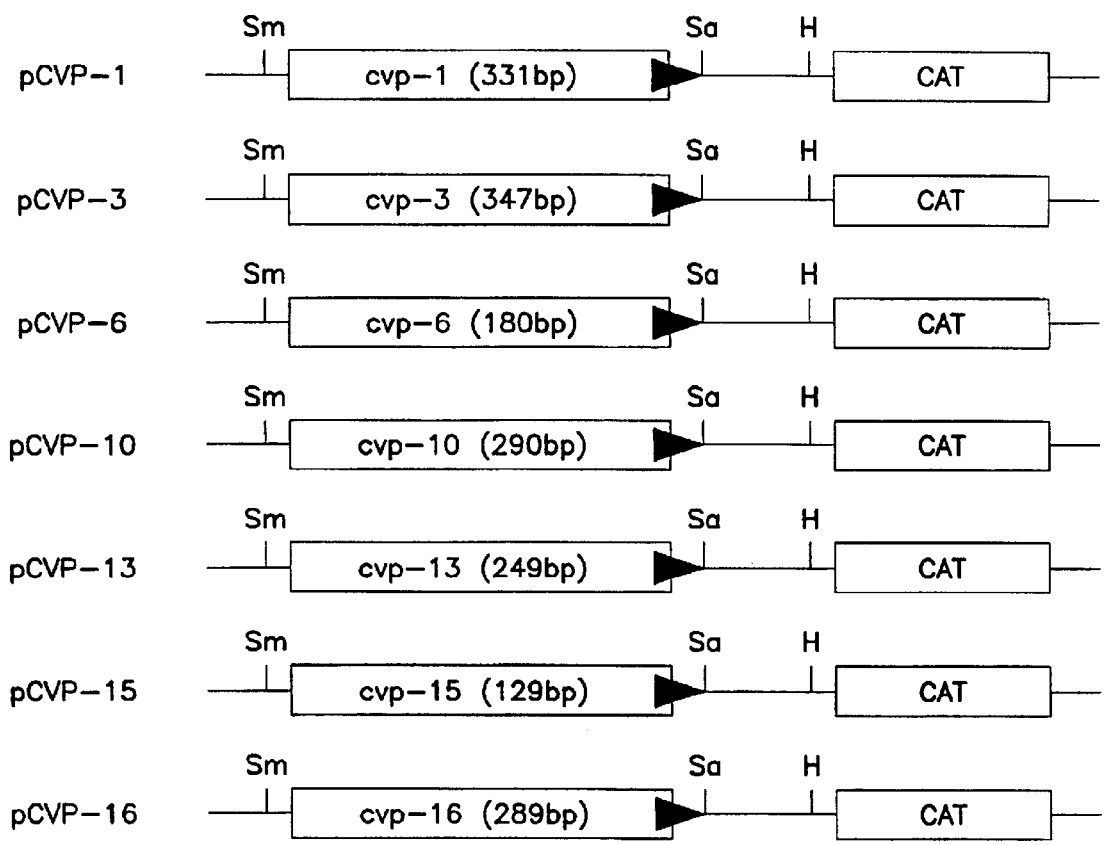
FIG. 2 is a diagrammatic representation of gene constructs using seven Chlorella virus promoters linked to the heterologous DNA sequence encoding the CAT protein.

The 36 transformants that showed a resistance to 500 μg/ml of chloramphenicol were further exposed to 500 μg, 700 μg, and 900 μg/ml chloramphenicol. Seven transformants showed normal growth in LB medium containing 700 μg/ml chloramphenicol and slower growth in the presence of 900 μg/ml chloramphenicol (FIG. 2).

Example 4

Comparison of CAT Activity Induced by Chlorella Virus Promoters

Figure 3:
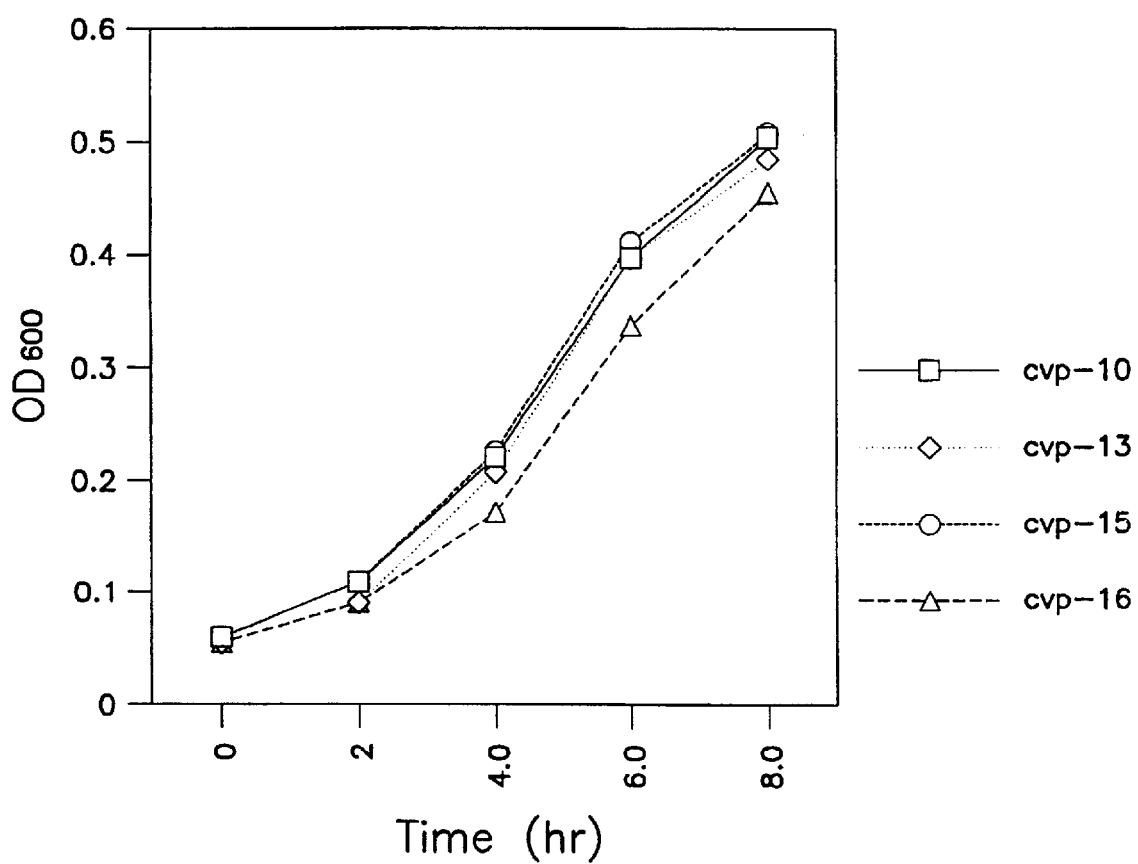
FIG. 3 is a comparison of CAT activities in chloramphenicol-resistant *E. coli* transformed with the CAT gene operably linked to the promoter sequences cvp-10, cvp-13, cvp-15 and cvp-16.

The CAT activity expressed by the chloramphenicol-resistant Chlorella virus promoter transformants of Example 3 was compared. Four of the seven chloramphenicol-resistant *E. coli* transformants, (CVP-10; CVP-13; CVP-15 and CVP-16) were grown in the presence of 600 μg/ml of chloramphenicol. Cell growth was monitored by measuring cell density ($OD_{600}$) at various times. As shown in FIG. 3, the four transformants displayed similar cell growth, indicating that similar levels of CAT activity was expressed in each culture.

Example 5

Purification of Plasmid DNA

Plasmid DNA was purified from those colonies showing the highest level of chloramphenicol resistance (700 to 900 µg/ml) using the Wizard miniprep plasmid DNA purification kit (Promega Co., Madison, Wis.) or Qiagen DNA purification kit (Qiagen Inc., Chatsworth, Calif.). Analysis of the plasmids by restriction endonuclease digestion indicated that all plasmids carried a DNA insert fragment.

The plasmids were digested with SmaI and HindIII and electrophoresed on 7.5% polyacrylamide gel or 0.8% agarose gel. The electrophoretic gel showed the seven viral promoter fragments ranged in size from 100 to 400 bp, as shown diagrammatically in FIG. 2.

Example 6

Sequencing Promoter Fragments

The seven promoter-containing viral DNA fragments (cvp-1, cvp-3, cvp-6, cvp-10, cvp13, cvp-15, and cvp-16) were excised from the pKK232-8 vector with SmaI and HindIII and subcloned into pUC19 or pBluescriptSK(+)II for sequencing. DNA sequencing was performed by the University of Nebraska Lincoln (UNL) sequencing lab using an automatic LICOR sequencer, sequences were determined in both directions using the Sanger dideoxy chain termination method.

| SEQ ID NO: | Chlorella Virus DNA Insert |
|---|---|
| 1 | cvp-1 |
| 2 | cvp-3 |
| 3 | cvp-6 |
| 4 | cvp-10 |
| 5 | cvp-13 |
| 6 | cvp-15 |
| 7 | cvp-16 |

Known *E. coli* promoter sequences contain 3 critical elements: two hexamer sequences (−35 region and −10 region) and a 16–18 bp spacing between these two regions. Using lac, lacUV5, trp, tac and PL promoter consensus sequences as references, −35 and −10 region putative sequences were assigned to each of the seven viral promoters. As shown below in Table I these hexamer sequences are either identical to, or only slightly different from, the consensus sequences of the known *E. coli* promoters. For example, the −35 sequence region of cvp-10 (TTGACA) or cvp-15(TTTACA) is identical to that found in trp (TTGACA) or lac (TATGTT).

Six of the seven isolated viral promoters of the invention have 16–18 bp spacing between the putative −35 and −10 regions. Both the cvp-13 viral promoter and the lac promoter have an identical −35 hexamer sequence (TTTACA), exactly the same spacing (18 bp) between the −35 and −10 regions, and a very similar −10 hexamer sequence (TACAAT for cvp-13 and TATAAT for lac).

| Promoter consensus | −35 Position TTGACA | −10 Position TATAAT | +position | SEQ.ID NO: |
|---|---|---|---|---|
| cvp-1 | CAAAAACAACTTGATGA | ATTTGACGAAGATGGGTATGATTTTTTTCAGGC | | 10 |
| cvp-3 | TCAGACGTGCTTGATAATAG | TGTGGAACTCGAGTATGATCCG | TCGACCT | 11 |
| cvp-6 | GCTTATCGTGTTGATATGATAAATGACAAAT | GATACGCTGTATCAACA | | 12 |
| cvp-10 | GCCCCGGTTCTTGACATTCTAAAAAAATGTGGAGTATCCTCGATCCGTCGA | | | 13 |
| cvp-13 | ATTTTAATTATTTACACCGGTTGTTGCTGAGTGATACAATGCAAATTCCCT | | | 14 |
| cvp-15 | AAAGCAATCCTTTACAATAC | TACAGAACGTGACTATATTATCAAAAAAGG | | 15 |
| cvp-16 | ACTGCCTCGTTATAAAGGTTAGTGAAAGCCATTGTATGTTATTACTGAGTT | | | 16 |
| lac | CACCCCAGGCTTTACACTTTATGCTTCCGGCTCGTATGTTGTG | TGGGATT | | 17 |
| lacUV5 | CACCCCAGGCTTTACACTTTATGCTTCCGGCTCGTATAATGTG | TGGAATT | | 18 |
| tzp | AAATGAGCTGTTGACAATTAATCATCGAACTA | GTTAACTAGTACGCAAGT | | 19 |
| tac | AAATGAGCTGTTGACAATTAATCAT | CGGCTCGTATAATGTG | TGGAATT | 20 |
| PL | TCTGGCGGTGTTGACATAAATACCACT | GGGGGTGATACTGAG | CACATCA | 21 |

"A" in bold type indicates the start site of transcription. Abbreviations: lac, the lac promoter; lacUV5, the lacUV5 promoter; trp, the trp promoter; tac, the tac promoter; PL, bacteriophage lamda PL promoter.

Sequence analysis of all seven Chlorella virus fragments revealed Sau3A1 sites at each end of the Chlorella virus inserts and flanking the multiple cloning sites of the pKK232-8 vector. The size of the DNA sequence for the seven promoter fragments coincided with the size of the restriction fragments determined by polyacrylamide gel electrophoresis.

Example 7

Comparing Promoter Activity of cvp-13 and tac

The tac promoter is a very strong *E. coli* promoter (de Boer, et al., 1983, *Proc. Natl. Acad. Sci.* 80:21–25) that has been widely used for gene expression in both research and industry. To compare promoter activity of viral promoter cvp-13 and promoter activity of tac in the same assay system, a promoter plasmid of tac was constructed using pKK232-8.

Figure 4:
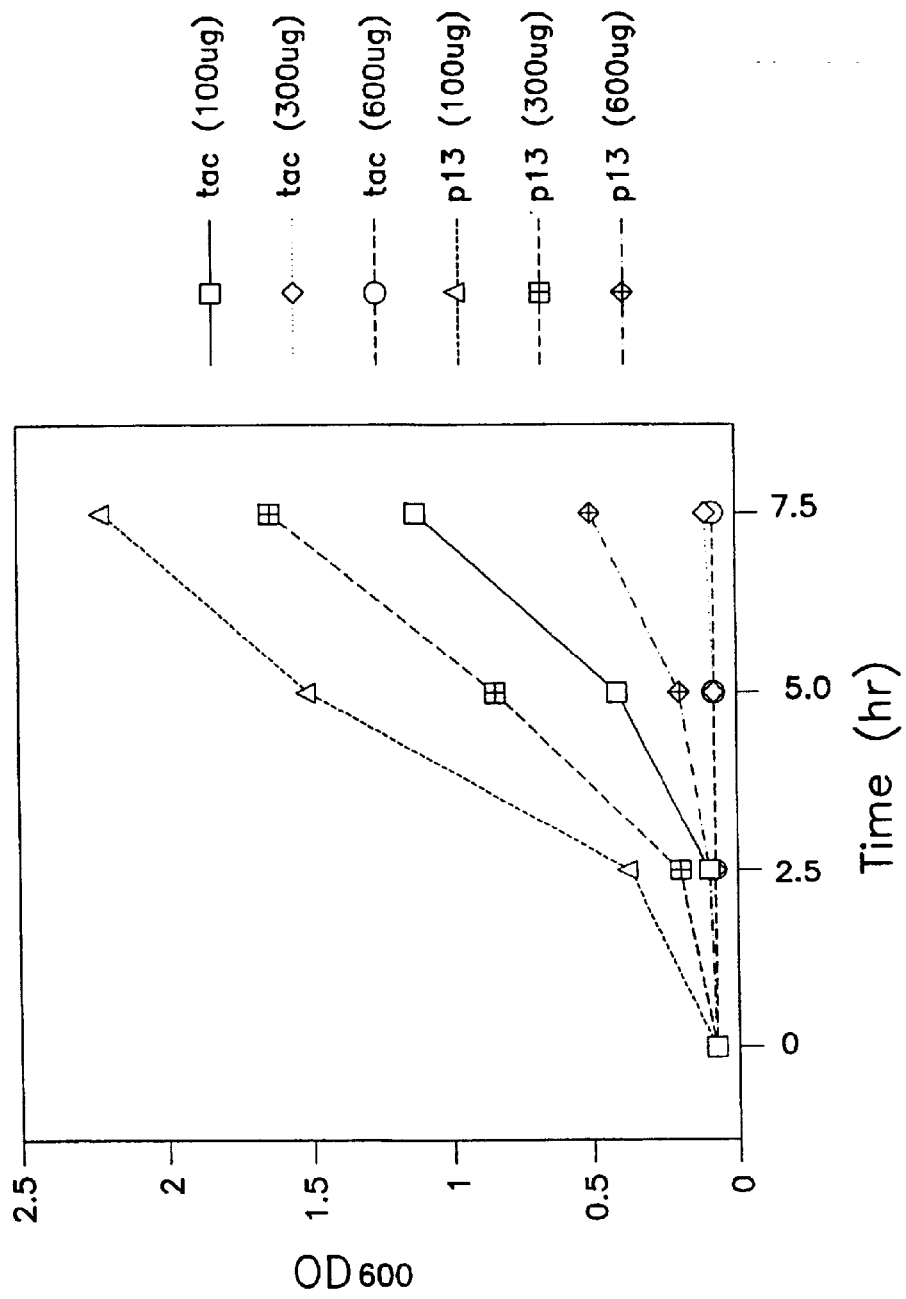
FIG. 4 is a comparison of promoter activities of the Chlorella virus promoter cvp-13 and the tac promoter transformed in to *E. coli* HB101 and grown in the presence of varying concentrations of chloramphenicol.

Two complementary oligomers containing the tac sequence,

5'-GGGAAATGAGCTGTTGACAATTAATCATGGC TCGTATAATGTGTGGAAGCTT-3' [SEQ ID NO: 8] and
5'-CCCTTTACTCGACAACTGTTAATTAGTAGCCGA GCATATTACACACCTTCG-3' [SEQ ID NO: 9]

were annealed and inserted in pKK232-8 upstream of the CAT gene, between SmaI and HindIII. The resulting plasmid, pTAC-cat, was transformed into *E. coli* HB101. Cells containing either pTAC-cat or pCVP-13 were grown in the presence of 100, 300 or 600 µg/ml of chloramphenicol. Antibiotic resistance was monitored by measuring cell growth densities at various times. As shown in FIG. 4, at all three levels of chloramphenicol concentration, the cvp-promoter showed higher promoter activity than the tac promoter.

Example 8

Construction of Regulated Viral Promoters

The 7 viral promoter fragments isolated from Chlorella viral genomes showed strong promoter activity in *E. coli*. However, their promoter activity was not regulated and, thus, could only constitutively direct protein expression. An approach for converting a constitutive promoter to an inducible promoter by fusing the promoter with the lac operator has been developed for a few promoters such as ribosomal RNA gene promoters (Brosius and Holy, 1984, *PNAS USA* 81:6929–6933) and the lipoprotein gene promoter (Nakamura, et al., 1982, *EMBO J.* 1:771–775). These modified hybrid promoters are repressed by the lac I gene product, lac repressor, whose specific binding to lac operator inhibits the start of transcription and is derepressed by an inducer such as isopropyl b-D-thiogalactoside (IPTG), which prevents the repressor protein from binding to the lac operator.

The lac operator was fused to the Chlorella viral promoters cvp-1, cvp-15 and cvp-16 to assess if the Chlorella viral promoters might be made inducible. Two complementary oligonucleotides containing the lac operator sequence and suitable restriction cloning sites were chemically synthesized by Operon Technology Inc. (Alameda, Calif.). The sequence of these oligos shown below:

5'-TCGACCGGGTACCTCGCGAGGAATTGTGAGCG GATAACAATTCCTCTAGA-3' [SEQ ID NO: 22]
5'-AGCTTCTAGAGGAATTGTTATCCGCTCACAATTCC TCGCGAGGTACCCGG-3' [SEQ ID NO: 23]

After denaturation and annealing the resulting oligo duplex was inserted downstream of the viral promoters at SAlI and HindIII sites on pKK232-8. The pKK232-8 clones containing a viral promoter/operator hybrid upstream of the CAT gene was transformed into *E. coli* HB101, which lacks lacI function. Similar levels of promoter activity as that observed for a viral promoter lacking the lac operator was detected by measuring resistance of the transformed cells to chloramphenicol. This suggested the manipulation of the viral promoters by fusing with lac operator did not cause reduction of promoter strength. The lac operator-fused promoters cvp-1, cvp-15 and cvp-16 were designed YX-1, YX-15 and YX-16, respectively.

Example 9

Expression of Glucagon-like Peptide (GLP-1) from a YX-15 Expression Vector

A. Construction of a YX-15 Expression Vector, pBN115-glp

To subclone the viral promoters (YX-1, YX-15 and YX-16) into an expression vector (which required restriction sites BglII and XbaI for cloning), the promoter fragments were modified by the polymerase chain reaction (PCR) using the following oligos synthesized by the Operon Technology Inc.:

5'-GGGTTCGAAGATCTAATTCCCGGGGATC-3' [SEQ ID NO: 24] and
5'-TGCATTTCTAGAATTGTGAATTGTTATCCGCTCA-3' [SEQ ID NO: 25].

Plasmid pGEX-2T was purchased from Pharmacia Biotech Inc. (piscataway, N.J.), which carries the pBR322 replication origin, lacIq gene, ampicillin resistance gene, and a tac promoter/glutathione S-transferase (GST) fusion gene expression cassette. The tac/GST cassette on pGEX-2T was first deleted by digested with FspI and SmaI to remove the 1.2 kb FspI-SmaI fragment and then replaced with a DNA fragment containing BglII/XbaI/NheI/XhoI sites, which can be used as cloning sites. The resulting plasmid was designed pBN115.

Figure 5:
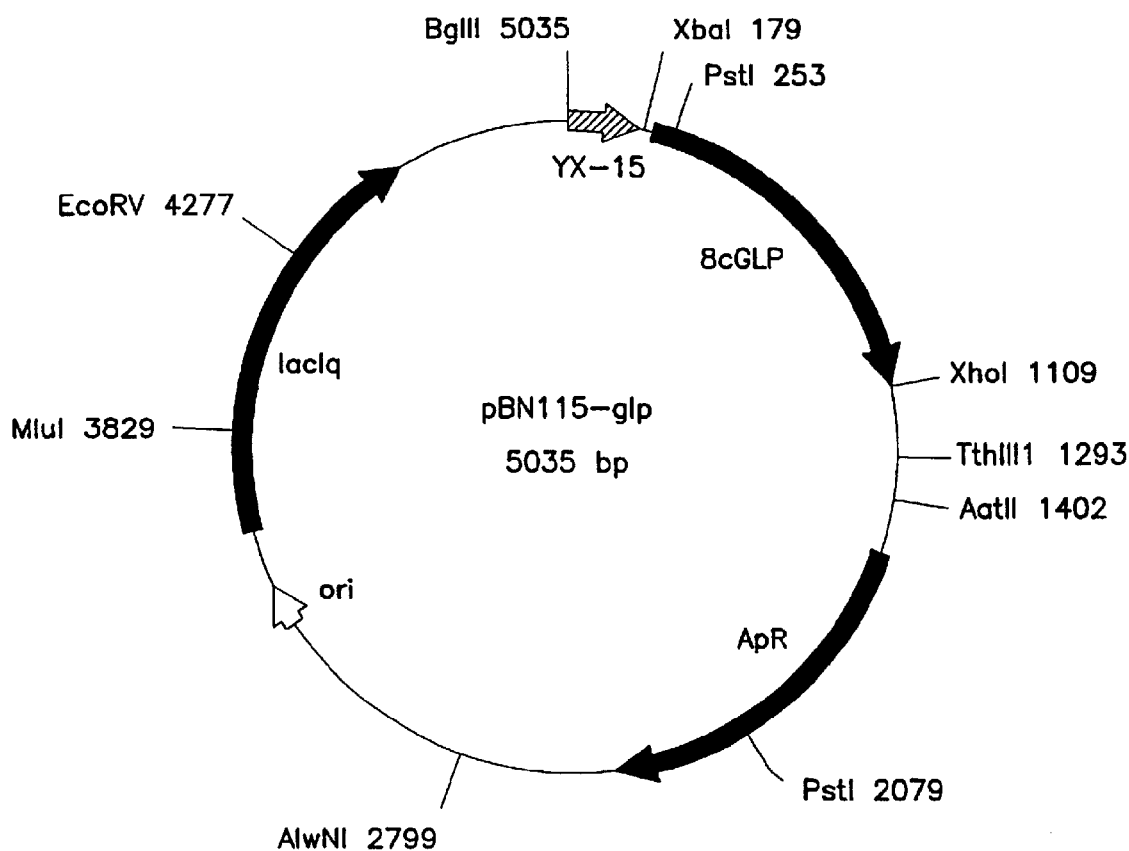
FIG. 5 is a diagrammatic representation of the pBN115-glp plasmid map.
Figure 9:
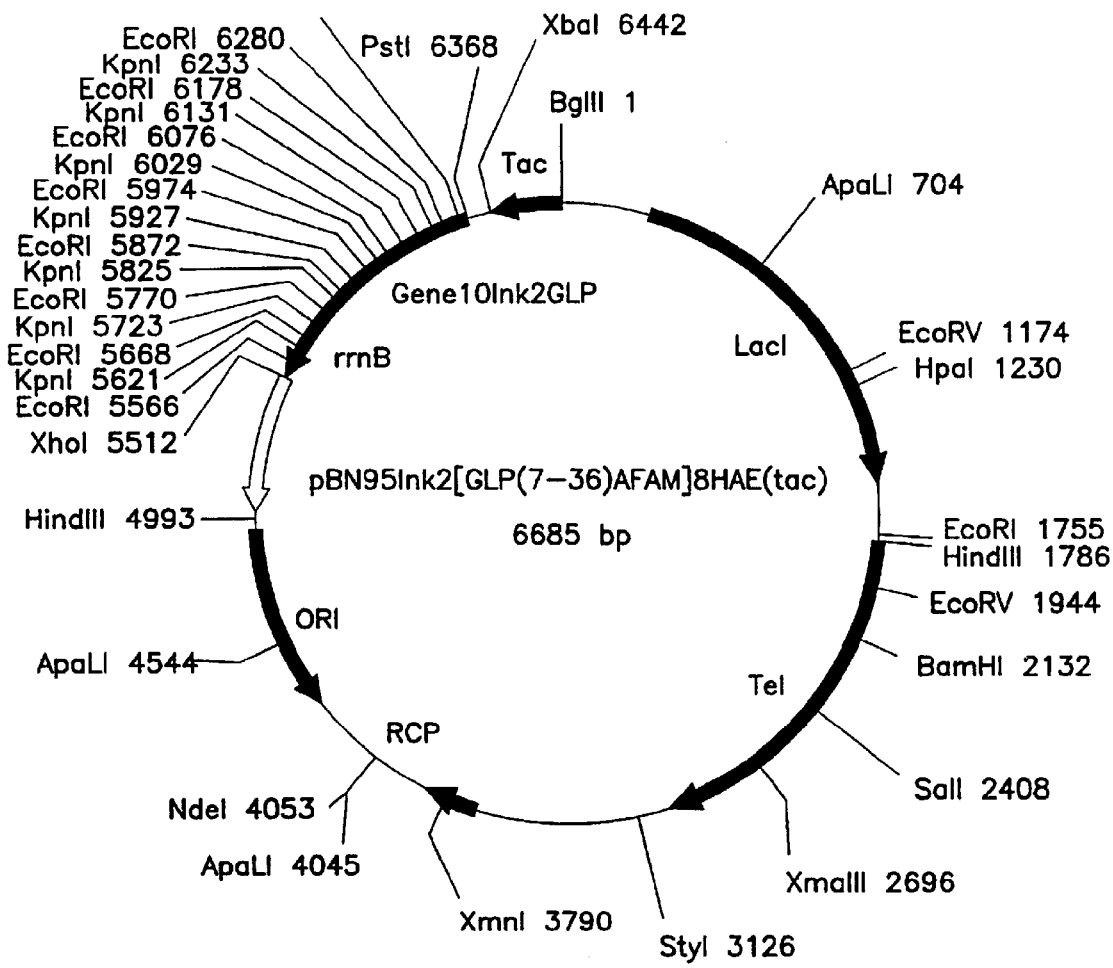
FIG. 9 is a diagramatic representation of the plasmid map of pBN95lnk2[GLP(7-36)AFAM]8HAE(tac).

GLP-1 is a 29 residue hormone peptide. A synthetic 8 copy GLP-1 gene was constructed and expressed in *E. coli*. To test GLP-1 expression under the control of YX-15, a YX-15/GLP-1 expression cassette was constructed by fusing a BglII-XbaI fragment containing YX-15 to an XbaI-XhoI fragment containing a ribosome binding site and the 8 copy GLP-1 gene. The YX-15/GLP-1 expression cassette was then inserted into pBN115 at the unique BglII and XhoI sites to generate pBN115-glp (FIG. 5). As a control expression vector, pBN115-glp/tac was constructed by replacement of YX-15 at BglII and XbaI sites on pBN115-glp with the tac promoter containing lac operator. The tac promoter can also be tightly regulated by IPTG.

B. Expression of GLP-1

Both p'BN115-glp and pBN115-glp/tac were transformed into *E. coli* host strain HMS174 (Novagen, Inc., Milwaukee, Wis.) in the presence of ampicillin. Expression of GLP-1 was induced with 0.1 to 2 mM IPTG at 37° C. to 21° C. Cells were harvested 15 hours post induction. Total cellular protein was prepared for SDS-PAGE analysis (FIG. 6). Production of GLP-1 was evaluated by gel scanning using the Personal Color Scanner and Adobe photoshop and NIH Image Analysis computer programs. As shown in Table 1, gel scanning revealed that expression level of GLP-1 from pBN115-glp at 37° C. was more than 46% of total cellular protein compared to 35% of total cellular protein from pBN115-glp/tac. One O.D.$_{600}$ of cells produced 40% more GLP-1 from pBN115-glp than ftom pBN115-glp/tac. The results clearly demonstrate the potential application of YX-15 as a very strong promoter for high-level recombinant protein production in *E. coli*.

TABLE 1

YX-15 - Directed GLP-1 Expression in *E. coli*

| | Reading of the intensity of the GLP-1 protein band | |
|---|---|---|
| Induction | tac | YX-15 |
| Uninduced | 84 | 385 |
| | (7%) | (35%) |
| 37° C. | 1089 | 1544 |
| | (100%) | (141%) |
| 27° C. | 55 | 1248 |
| | (5%) | (114%) |
| 21° C. | ND | 830 |
| | | (76%) |

For each treatment, total protein was extracted from 0.25 O.D.$_{600}$ of cells and analyzed on a 16% PAGE gel (FIG. 6).

After staining with Coomassie blue, intensity of protein bands were scanned using Personal Color Scanner and Adobe Photoshop and NIH Image Analysis computer programs. Percentage in parenthesis represents an expression level of GLP-1 relative to the expression level of GLP-1 driven by the tac promoter at 37° C.

C. Induction by IPTG

Although a basal expression level of GLP-1 in HMS174 harboring pBN115-glp was detectable in the absence of IPTG, GLP-1 expression level showed 4-fold increase after addition of IPTG. In contrast, IPTG induced 13-fold increase in GLP-1 production from pBN115-glp/tac. This suggested that GLP-1 expression from pBN115-glp does respond to IPTG induction. Regulation of GLP-1 expression from pBN115-glp, however, was less tight than that from pBN115-glp/tac.

Inducibility of IPTG at various concentrations (0,0.25, 0.5, 1.0 and 2.0 mM) were tested for GLP-1 expression at 37° C. A similar high level of GLP-1 production was observed from pBN115-glp within the IPTG concentration range of 2 mM and 0.1 mM. This suggested a concentration of IPTG as low as 0.1 mM was sufficient to induce GLP-1 overexpression.

At all tested IPTG concentrations, GLP-1 production from pBN115-glp was consistently higher than GLP-1 production from pBN115-glp/tac, suggesting higher promoter activity from YX-15 compared to tac.

D. Effect of Temperature

Cultivation temperature critically affects microbe performance. An induction temperature of 37° C. is commonly used for satisfactory recombinant protein production in *E. coli*, whereas lower temperatures, in some cases, show the advantage for producing active proteins and avoiding the formation of inactive protein aggregates. However, at lower temperatures, the rates of transcription and translation, being biochemical reactions, will be greatly slowed down and, thus, the final yield of the target protein will be reduced. Therefore, the use of a promoter highly active at lower temperatures will be necessary for high-level protein production. Prior to the instant invention, such an *E. coli* promoter was not available. Commonly used promoters such as the tac promoter and the T7 promoter are very active at 37° C., but much weaker at lower temperatures, as described below by the data for the tac promoter.

The promoter activity of YX-15 at the temperature range of 37° C. and 21° C. was compared in controlling GLP-1 production. The results shown in Table 1 (above) confirm that the YX-15 promoter was able to drive a high level of GLP-1 expression at the temperature range from 37° C. to 21° C. Expression levels using the YX-15 promoter at 27° C. were even slightly higher than with the tac promoter at 37° C. The reduction in the GLP-1 expression level driven by YX-15 at 27° C. and at 21° C. as compared with at 37° C. was 20% and 50%, respectively. In contrast, a 95% drop in expression using the tac was observed at 27° C. as compared with at 37° C. Protein expression of the tac promoter at 21° C. was not detected.

Example 10

Function of the Viral Promoters in Plants

To test if the isolated viral promoters finction in plants, the 7 promoter fragments were inserted into the β-glucuronidase (GUS) expression vector pBI221 (Clotech Laboratories, Inc., Palo Alto, Calif.) upstream of the GUS gene to replace CaMV 35S promoter. The resulting plasmids were introduced into tobacco leaves and wheat immature embryos by the method of microprojectile bombardment. The transformed explants were then assayed for GUS expression histochemically by counting the formation of blue GUS foci on the explants tested. Positive control explants were transformed with pBI221, which contains the CAMV 35S promoter.

As shown in Table 2, positive results from the GUS transient assay were observed with the promoter cvp-15, but not for the other 6 promoters.

TABLE 2

| Vector | Range of Mean GUS Foci/Explant/Plat* | |
|---|---|---|
| | Tobacco | Wheat |
| pBI221 (CaMV 35S) | 2.6–9.5 | 7.6–17.2 |
| pBI221-YX15 | 0.7–1.5 | 0.4–1.6 | n = 3 experiments

Example 11

Low Temperature Expression of GLP Constructs with pYX16

The expression plasmid pBN115-glp (8 copy GLP-1) described above for Example 9 drives expression of the 8 copy GLP-1 (7-36) expression cassette using the YX15 promoter (cvp-15 plus lac operator). A second plasmid containing the YX16 promoter (cvp-16 plus lac operator) and 3 copy GLP-1(7-36) was constructed by replacement of the BglII/Xbal promoter fragment in the pBN115 vector with that fragment from the YX-16 promoter. The 8 copy GLP-1 cassette was also replaced with the 3 copy GLP-1 cassette by substitution of the XbaI-XhoI fragment. This construct, pGEXlnk2 (3copy GLP)YX16 contains the same plasmid backbone as pBN115, except that the promoter is YX16 rather than YX15.

A YX16 promoter construct driving 8 copy GLP-1(7-36) expression was also made, using the pBN53 expression plasmid. The YX16 promoter was cloned into this construct as a BglII/Xbal fragment. The resulting plasmid, pBN53lnk28copyGLP YX16, is tetracycline resistant and contains the lacIq gene to repress uninduced expression. The pBN95 plasmid is identical to the pBN53 plasmid, except that it contains the lac I gene, rather than the lacIq gene. This change results in a lower level of expression oflhe Lac I gene product in pBN95, and consequently, a lower level of repression of uninduced protein levels using this vector.

The expression vectors were transformed into *E. coli* cells using the methods and materials described above for Example 9. Expression of GLP-1 was induced with IPTG as described for Example 9, at temperatues of 27° C. and 37° C.

Protein samples taken from cell cultures after induction of tac or YX16 promoter controlled 3 copy GLP-1(7-36) and 8 copy GLP-1(7-36) were separated on a 16% TrisTricine SDS-PAGE gel and stained with Coomassie blue.

The data, shown in FIG. 7, demonstrates that the YX16 promotor functions well at 27° C., while the tac promoter is inactive at this temperature. The GLP precursor peptide is soluble at 27° C., but insoluble at 37° C.

The data, shown in FIG. 8, demonstrates that both the YX15 and YX16 promoters function at 27° C., while the tac promoter is inactive at this temperature. The data demonstrates that YX16 promoter functions at low temperatures (27° C.), with two independent target peptides.

The above specification, examples and data provide a complete description of the manufacture and use of the composition of the invention. Since many embodiments of the invention can be made without departing from the spirit and scope of the invention, the invention resides in the claims hereinafter appended.

I claim:

1. An isolated DNA molecule comprising a polynucleotide having the sequence of SEQ ID NO: 1.

2. An isolated DNA molecule comprising a polynucleotide having the sequence of SEQ ID NO: 2.

3. An isolated DNA molecule comprising a polynucleotide having the sequence of SEQ ID NO: 3.

4. An isolated DNA molecule comprising a polynucleotide having the sequence of SEQ ID NO: 4.

5. An isolated DNA molecule comprising a polynucleotide having the sequence of SEQ ID NO: 5.

6. An isolated DNA molecule comprising a polynucleotide having the sequence of SEQ ID NO: 6.

7. An isolated DNA molecule comprising a polynucleotide having the sequence of SEQ ID NO: 7.

8. A host cell comprising a gene construct comprising a promoter operably linked to a structural gene, said promoter comprising the nucleotide sequence of SEQ ID NO: 1, 2, 3, 4, 5, 6, or 7, wherein said host cell is an *E. coli* cell selected from the group consisting of HB101, JM109, BL21 and HMS174.

9. An isolated, inducible promoter comprising the nucleic acid sequence set forth as SEQ ID NO: 1, 2, 3, 4, 5, 6, or 7.

10. An isolated, inducible promoter comprising the nucleic acid sequence set forth as SEQ ID NO: 1, 2, 3, 4, 5, 6, or 7 operatively linked to a lac operator.

11. A gene construct comprising:

a promoter comprising the nucleic acid sequence set forth as SEQ ID NO: 1, 2, 3, 4, 5, 6, or 7;

a lac operateor; and a structural gene, wherein the promoter, operator, and structural gene are operatively linked.

12. A gene construct comprising:

a promoter comprising the nucleic acid sequence set forth as SEQ ID NO: 15;

a lac operator; and a structural gene, wherein the promoter, operator, and structural gene are operatively linked.

13. The gene construct of claim 11, wherein the structural gene comprises a nucleic acid sequence encoding glucagon-like peptide 1, growth hormone releasing factor, parathyroid hormone, carbonic anhydrase, beta-galactosidase, chloramphenicol acetyltransferase, or glutathione acetyltransferase.

14. A host cell comprising the gene construct of claim 11.

15. The host cell of claim 14, wherein the host cell is a prokaryotic cell.

16. The host cell of claim 15, wherein the prokaryotic cell is an *E. coli* cell.

17. The host cell of claim 14, wherein the host cell is a plant cell.

18. A process for producing a protein in a host cell, comprising:

(A) transforming a host cell with a gene construct comprising a promoter comprising the nucleic acid sequence set forth as SEQ ID NO: 1, 2, 3, 4, 5, 6, or 7, a lac operator, and a structural gene, wherein the promoter, operator and structural gene are operatively linked; and (B) culturing the host cell under conditions whereby the protein is expressed.

19. The process of claim 18, wherein the transformed host cell is incubated at less than 37° C.

20. The process of claim 18, wherein the transformed host cell is incubated at a temperature in the range of 21 to 37° C.

21. The process of claim 18, wherein the transformed host cell is incubated at a temperature in the range of 21 to 30° C.

22. The inducible promoter of claim 10, wherein said promoter operates in a range of 21 to 37° C.

23. The inducible promoter of claim 10, wherein said promoter operates at a temperature below 37° C.

* * * * *

```
                              SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
         (A) LENGTH: 358 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 1:

CCCGGGGATC GCAGGGCATG GGCATTAAAA GAACTTTATG GAATCAAAAA TCTTAGTGAA      60

TTTCCACCAC AGGTATATAG TCTTCAGGAC GCTAACGATG ATATCAACGA TTGTATCAAA     120

GGTTATCGTT TGAGGCACTC ATATCAGGTA GTTTCTACAC AGAAACTTGA ACAACGCCTG     180

GGAAAAGATC CTGAGCATAG TAACTTATAT ACTAGCAGAT GTTGTAACGA TGCTTTATAT     240

GAATATGAAT TAGCACAACG ACAACTACAA AAACAACTTG ATGAATTTGA CGAAGATGGG     300

TATGATTTTT TTCAGGCACG TATAAATACA TTAGATCCGT CGACCTGCAG CCAAGCTT      358

(2) INFORMATION FOR SEQ ID NO: 2:

(i) SEQUENCE CHARACTERISTICS:
         (A) LENGTH: 374 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 2:

CCCGGGGATC TAATTCAGGG TGCGAATTTC TTGAACATCA AAGGTCTGTT GGACGTTTTG      60

TGTGCAGCGG TTGCTGATCG CATTGAATCC ATCAATAAAC AGATTGGGGT AAATATCAAA     120

CCCAGTTAGT CGGACATTAG AAGGATTTGT GAGACCACCA CATCCAACGA CACCTAATGG     180

TGTTGTGAAT GATATATTAG AAATGTTACT TATCATTGAT ATTTGCATAA CACCATTTCC     240

CTTTGCTTGA TTTCTACCTA TACTAATTGA TTGTATTGTA GTGCACGCGG CGTACTTACT     300

TGTATTTGCC GTCTCAGACG TGCTTGATAA TAGTGTGGAA CTCGAGTATG ATCCGTCGAC     360

CTGCAGCCAA GCTT                                                       374

(2) INFORMATION FOR SEQ ID NO: 3:

(i) SEQUENCE CHARACTERISTICS:
         (A) LENGTH: 207 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 3:

CCCGGGGATC ATCGAAAGCA ACTGCCGCAT TCGAAACTTC GACTGCCTCG TTATAAAGGT      60
```

-continued

```
TAGTGAAAGC CATTGTATGT TATTACTGAG TTATTTAATT TAGCTTGCTT AAATGCTTAT      120

CGTGTTGATA TGATAAATGA CAAATGATAC GCTGTATCAA CATCTCAAAA GATTAATACG      180

AAGATCCGTC GACCTGCAGC CAAGCTT                                          207
```

(2) INFORMATION FOR SEQ ID NO: 4:

(i) SEQUENCE CHARACTERISTICS:
        (A) LENGTH: 317 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

```
CCCGGGGATC GTTTCTCAGG GCGTCCGGGA GCATATTTCA GACTTGTCCA GCCGTATGAG      60

CATCACGTGC GCGTTCCTAG CAAGAGCGTG TACGTATATT CTTTCGCTCT AGAAGATGCA     120

GATTCGAGAC AACCGAATGG ATCGAATCTA TTTGTACCCC GATATATATA GAATCTAGTC     180

TAAACAAAAC GACCGCGGCT CTTGCCAATA AATGTGACGC AATTAACGCA TTCGTGAATG     240

ATGACTTGTC CGCCCCGGTT CTTGACATTC TAAAAAAATG TGGAGTATCC TCGATCCGTC     300

GACCTGCAGC CAAGCTT                                                    317
```

(2) INFORMATION FOR SEQ ID NO: 5:

(i) SEQUENCE CHARACTERISTICS:
        (A) LENGTH: 277 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

```
CCCGGGGATC TGCGTATTGC GGGACTTTTG AGCATTTTCC AGAACGGATT GCCGGGACGT      60

ATACTGAACC TCCAGTCCCT TGCTCGTCG TATTTCCCAT AATATACATA TACACTATTT      120

TAATTATTTA CACCGGTTGT TGCTGAGTGA TACAATGCAA ATTCCCTCCA CCGAGGAGGA     180

TCGCGAACTG TCCAAATGTC TTCTTTCTGC AGCTCCATAC GGAGTCGTTA GGAAACATTC     240

ACTTAATTAT AGGATCCGTC GACCTGCAGC CAAGCTT                              277
```

(2) INFORMATION FOR SEQ ID NO: 6:

(i) SEQUENCE CHARACTERISTICS:
        (A) LENGTH: 181 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

```
CCCGGGGATC AGGCCTCGCT TATAAATATG GTATTGATGT ACTTGCCGGT GTGATTGACT      60

CAGATTACAG AGGAGAGTTG AAAGCAATCC TTTACAATAC TACAGAACGT GACTATATTA     120

TCAAAAAAGG CGATCAGCCA AGCTTCGTCG ACCTGCGATC CGTCGACCTG CAGCCAAGCT     180

T                                                                    181
```

(2) INFORMATION FOR SEQ ID NO: 7:

(i) SEQUENCE CHARACTERISTICS:

(A) LENGTH: 316 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

CCCGGGGATC GCAAAACTCA CAGTCAACAA ACCAAAACAC GGAATGAAGA AAGGAGAAAC    60

TGTGATCATG TGGCAACAAG ATGGAGGTGT CATAGACTAC ATTTACCCTC CCTCTGATCA   120

TCGAAAGCAA CTGCCGCATT CGAAACTTCG ACTGCCTCGT TATAAAGGTT AGTGAAAGCC   180

ATTGTATGTT ATTACTGAGT TATTTAATTT AGCTTGCTTA AATGCTTATC GTGTTGATAT   240

GATAAATGAC AAATGATACG CTGTATCAAC ATCTCAAAAG ATTAATACGA AGATCCGTCG   300

ACCTGCAGCC AAGCTT                                                  316

(2) INFORMATION FOR SEQ ID NO: 8:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

GGGAAATGAG CTGTTGACAA TTAATCATGG CTCGTATAAT GTGTGGAAGC TT            52

(2) INFORMATION FOR SEQ ID NO: 9:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

CCCTTTACTC GACAACTGTT AATTAGTAGC CGAGCATATT ACACACCTTC G             51

(2) INFORMATION FOR SEQ ID NO: 10:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

CAAAAACAAC TTGATGATTT GACGAAGATG GGTATGATTT TTTTCAGGC                49

(2) INFORMATION FOR SEQ ID NO: 11:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

TCAGACGTGC TTGATAATAG TGTGGAACTC GAGTATGATC CGTCGACCT        49

(2) INFORMATION FOR SEQ ID NO: 12:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

GCTTATCGTG TTGATATGAT AAATGACAAA TGATACGCTG TATCAACA        48

(2) INFORMATION FOR SEQ ID NO: 13:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

GCCCCGGTTC TTGACATTCT AAAAAAATGT GGAGTATCCT CGATCCGTCG A     51

(2) INFORMATION FOR SEQ ID NO: 14:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

ATTTTAATTA TTTACACCGG TTGTTGCTGA GTGATACAAT GCAAATTCCC T     51

(2) INFORMATION FOR SEQ ID NO: 15:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

AAAGCAATCC TTTACAATAC TACAGAACGT GACTATATTA TCAAAAAGG        50

(2) INFORMATION FOR SEQ ID NO: 16:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

ACTGCCTCGT TATAAAGGTT AGTGAAAGCC ATTGTATGTT ATTACTGAGT T     51

(2) INFORMATION FOR SEQ ID NO: 17:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

CACCCCAGGC TTTACACTTT ATGCTTCCGG CTCGTATGTT GTGTGGAATT        50

(2) INFORMATION FOR SEQ ID NO: 18:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

CACCCCAGGC TTTACACTTT ATGCTTCCGG CTCGTATAAT GTGTGGAATT        50

(2) INFORMATION FOR SEQ ID NO: 19:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

AAATGAGCTG TTGACAATTA ATCATCGAAC TAGTTAACTA GTACGCAAGT        50

(2) INFORMATION FOR SEQ ID NO: 20:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

AAATGAGCTG TTGACAATTA ATCATCGGCT CGTATAATGT GTGGAATT          48

(2) INFORMATION FOR SEQ ID NO: 21:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 21:

TCTGGCGGTG TTGACATAAA TACCACTGGG GGTGATACTG AGCACATCA         49

(2) INFORMATION FOR SEQ ID NO: 22:

(i) SEQUENCE CHARACTERISTICS:
        (A) LENGTH: 50 base pairs
        (B) TYPE: nucleic acid (C) STRANDEDNESS: single
            (D) TOPOLOGY: linear (ii) MOLECULE TYPE: cDNA (xi) SEQUENCE DESCRIPTION: SEQ ID NO: 22:

TCGACCGGGT ACCTCGCGAG GAATTGTGAG CGGATAACAA TTCCTCTAGA                50

(2) INFORMATION FOR SEQ ID NO: 23:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 23:

AGCTTCTAGA GGAATTGTTA TCCGCTCACA ATTCCTCGCG AGGTACCCGG                50

(2) INFORMATION FOR SEQ ID NO: 24:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 24:

GGGTTCGAAG ATCTAATTCC CGGGGATC                                        28

(2) INFORMATION FOR SEQ ID NO: 25:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 25:

TGCATTTCTA GAATTGTGAA TTGTTATCCG CTCA                                 34